US008563017B2

(12) United States Patent
Cunningham et al.

(10) Patent No.: US 8,563,017 B2
(45) Date of Patent: Oct. 22, 2013

(54) DISINFECTANT WET WIPE

(75) Inventors: Corey Thomas Cunningham, Larsen, WI (US); Victoria Elizabeth Encisco, Marietta, GA (US); Frances Luella Walsh, Atlanta, GA (US); Gu Lou, Roswell, GA (US); Ali Yahiaoui, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 332 days.

(21) Appl. No.: 12/334,755

(22) Filed: Dec. 15, 2008

(65) Prior Publication Data

US 2009/0285871 A1  Nov. 19, 2009

Related U.S. Application Data

(60) Provisional application No. 61/053,360, filed on May 15, 2008.

(51) Int. Cl.
*A01N 25/34* (2006.01)
*A01N 37/00* (2006.01)
*A01P 1/00* (2006.01)

(52) U.S. Cl.
USPC .......................................... 424/405; 514/557

(58) Field of Classification Search
None
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo et al. |
| 3,635,828 A | 1/1972 | Benjamin et al. |
| 3,692,618 A | 9/1972 | Dorschner et al. |
| 3,802,817 A | 4/1974 | Matsuki et al. |
| 3,849,241 A | 11/1974 | Butin et al. |
| 4,041,203 A | 8/1977 | Brock et al. |
| 4,100,324 A | 7/1978 | Anderson et al. |
| 4,130,501 A | 12/1978 | Lutz et al. |
| 4,144,370 A | 3/1979 | Boulton |
| 4,340,563 A | 7/1982 | Appel et al. |
| 4,374,888 A | 2/1983 | Bornslaeger |
| 4,640,810 A | 2/1987 | Laursen et al. |
| 4,663,220 A | 5/1987 | Wisneski et al. |
| 4,766,029 A | 8/1988 | Brock et al. |
| 5,213,881 A | 5/1993 | Timmons et al. |
| 5,259,848 A | 11/1993 | Terry et al. |
| 5,284,703 A | 2/1994 | Everhart et al. |
| 5,350,624 A | 9/1994 | Georger et al. |
| 5,382,400 A | 1/1995 | Pike et al. |
| 5,451,346 A | 9/1995 | Amou et al. |
| 5,527,892 A | 6/1996 | Borsotti et al. |
| 5,540,332 A | 7/1996 | Kopacz et al. |
| 5,656,302 A | 8/1997 | Cosentino et al. |
| 5,656,361 A * | 8/1997 | Vogt et al. ..................... 428/198 |
| 5,667,635 A | 9/1997 | Win et al. |
| 5,703,036 A | 12/1997 | Iakovides |
| 5,767,055 A | 6/1998 | Choy et al. |
| 5,770,543 A | 6/1998 | Garst et al. |
| 5,785,179 A | 7/1998 | Buczwinski et al. |
| 5,853,430 A | 12/1998 | Shindo et al. |
| 5,872,090 A | 2/1999 | You et al. |
| 5,888,524 A | 3/1999 | Cole |
| 5,895,504 A | 4/1999 | Sramek et al. |
| 5,900,187 A | 5/1999 | Scialla et al. |
| 5,900,256 A | 5/1999 | Scoville, Jr. et al. |
| 5,904,734 A | 5/1999 | Friberg et al. |
| 5,929,012 A | 7/1999 | Del Duca et al. |
| 5,962,112 A | 10/1999 | Haynes et al. |
| 5,964,351 A | 10/1999 | Zander |
| 5,997,585 A | 12/1999 | Scialla et al. |
| 6,001,794 A | 12/1999 | Del Duca et al. |

(Continued)

FOREIGN PATENT DOCUMENTS

EP  1059032 A1  12/2000
GB  2397823 A  8/2004

(Continued)

OTHER PUBLICATIONS

Product Information about Aerosol® OT Surfactants (Sodium Dioctyl Sulfosuccinate) from Cytec Industries, Inc., 2000, 6 pages.
Product Information about Synthrapol, 1998-2008, 5 pages.
English Abstract of JP2000144200, published May 26, 2000, European Patent Office.
Friedman et al. *Field Guide to Stains: How to Identify and Remove Virtually Every Stain Known to Man*, Quirk Publications, Inc. 2002: pp. 199-202.
Seeing Spots? Don't Rely on Quick Stain Removers, *Consumer Reports*, Aug. 2006, p. 9.
Stain Removers: Which are Best, *Consumer Reports*, Mar. 2000, p. 52.
Search Report and Written Opinion for PCT/IB2009/051381 dated Oct. 29, 2009, 14 pages.
Supplementary European Search Report dated Sep. 12, 2012, 6 pages.

*Primary Examiner* — David J Blanchard
*Assistant Examiner* — Garen Gotfredson
(74) *Attorney, Agent, or Firm* — Dority & Manning, P.A.

(57) ABSTRACT

A disinfectant wet wipe that contains a germicidal solution and a nonwoven web material is provided. The germicidal solution includes a peracid and peroxide, which can act synergistically together to be efficacious against pathogens when exposed thereto. To stabilize the solution over a period of time (e.g., during storage), a variety of aspects of the wipe are selectively controlled in accordance with the present invention. For example, the nonwoven web material used in the wipe is formed from a synthetic polymer and is relatively hydrophobic in nature. Without intending to be limited by theory, it is believed that such materials possess a lower reduction potential for peroxides/peracids than cellulosic-based materials. In this manner, significant degradation of the peroxide or peracid contained in the germicidal solution is limited. To improve the wettability of the nonwoven web material, one or more surfactants are also employed in the germicidal solution. Besides improving wettability, the present inventors have surprisingly discovered that certain surfactants may also improve the stability of the solution.

27 Claims, 1 Drawing Sheet

(56) References Cited

U.S. PATENT DOCUMENTS

| | | | |
|---|---|---|---|
| 6,028,018 A * | 2/2000 | Amundson et al. ............ 442/381 |
| 6,030,331 A | 2/2000 | Zander |
| 6,066,610 A | 5/2000 | Sramek |
| 6,158,614 A | 12/2000 | Haines et al. |
| 6,168,808 B1 | 1/2001 | Hamon Godin et al. |
| 6,171,346 B1 | 1/2001 | Yeazell et al. |
| 6,187,738 B1 | 2/2001 | Micciche et al. |
| 6,269,969 B1 | 8/2001 | Huang et al. |
| 6,269,970 B1 | 8/2001 | Huang et al. |
| 6,273,359 B1 | 8/2001 | Newman et al. |
| 6,277,105 B1 | 8/2001 | Rynish |
| 6,315,864 B2 | 11/2001 | Anderson et al. |
| 6,376,444 B1 | 4/2002 | Hortel et al. |
| 6,391,840 B1 | 5/2002 | Thompson et al. |
| 6,420,332 B1 | 7/2002 | Simpson |
| 6,437,199 B1 | 8/2002 | Oka et al. |
| 6,440,437 B1 | 8/2002 | Krzysik et al. |
| 6,471,728 B2 | 10/2002 | Smith et al. |
| 6,495,501 B1 | 12/2002 | Del Duca et al. |
| 6,524,379 B2 | 2/2003 | Nohr et al. |
| 6,579,838 B2 | 6/2003 | Housmekerides et al. |
| 6,644,879 B2 | 11/2003 | Irvin et al. |
| 6,653,269 B2 | 11/2003 | Housmekerides et al. |
| 6,689,730 B2 | 2/2004 | Hortel et al. |
| 6,730,819 B1 | 5/2004 | Pesce |
| 6,753,306 B2 | 6/2004 | Simpson |
| 6,790,380 B2 | 9/2004 | Sato et al. |
| 6,832,867 B2 | 12/2004 | Sandbach et al. |
| 6,838,423 B2 | 1/2005 | Irvin et al. |
| 6,846,332 B2 | 1/2005 | Boissie et al. |
| 6,846,793 B1 * | 1/2005 | Griese ......................... 510/421 |
| 6,946,413 B2 | 9/2005 | Lange et al. |
| 6,958,103 B2 | 10/2005 | Anderson et al. |
| 6,960,349 B2 | 11/2005 | Shantz et al. |
| 7,047,582 B2 | 5/2006 | Moe et al. |
| 7,148,187 B1 | 12/2006 | Simon et al. |
| 7,182,537 B2 | 2/2007 | Policicchio et al. |
| 7,320,956 B2 | 1/2008 | Johnson et al. |
| 7,390,431 B2 | 6/2008 | Faryniarz et al. |
| 7,442,678 B2 | 10/2008 | Sandbach et al. |
| 7,459,496 B2 | 12/2008 | Hsu et al. |
| 7,462,590 B2 | 12/2008 | Tichy et al. |
| 2002/0091070 A1 | 7/2002 | Englsch et al. |
| 2002/0174500 A1 | 11/2002 | Micciche et al. |
| 2003/0109411 A1 | 6/2003 | Kilkenny et al. |
| 2003/0119209 A1 | 6/2003 | Kaylor et al. |
| 2004/0161991 A1 * | 8/2004 | Walton et al. ................. 442/327 |
| 2004/0231061 A1 | 11/2004 | Irvin et al. |
| 2005/0019421 A1 * | 1/2005 | Hobbs et al. .................. 424/616 |
| 2005/0026802 A1 | 2/2005 | Kilkenny et al. |
| 2005/0159063 A1 | 7/2005 | Hill et al. |
| 2006/0008621 A1 | 1/2006 | Gusky et al. |
| 2006/0204530 A1 | 9/2006 | Ramirez et al. |
| 2006/0229225 A1 * | 10/2006 | Martin et al. ................. 510/375 |
| 2007/0001145 A1 | 1/2007 | Faryniarz et al. |
| 2007/0258915 A1 | 11/2007 | Kielbania |
| 2008/0132438 A1 | 6/2008 | Hoffman et al. |
| 2009/0061718 A1 | 3/2009 | Seidling et al. |
| 2009/0062172 A1 | 3/2009 | Cunningham et al. |

FOREIGN PATENT DOCUMENTS

| WO | WO 2004067194 A2 | 8/2004 |
| WO | WO 2004067194 A3 | 8/2004 |
| WO | WO 2006076334 A1 | 7/2006 |

* cited by examiner

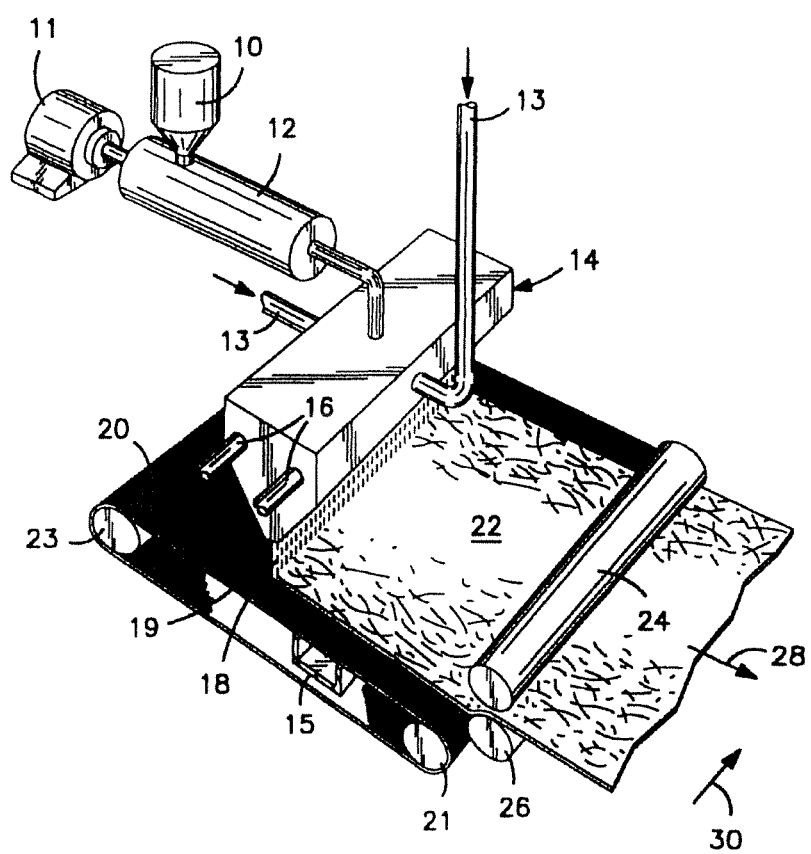

DISINFECTANT WET WIPE

RELATED APPLICATIONS

The present application claims priority to Provisional Application Ser. No. 61/053,360, which was filed on May 15, 2008.

BACKGROUND OF THE INVENTION

Solutions containing peroxides and peracids are well known in the industry for their germicidal (e.g., bactericidal, fungicidal, virucidal, tuberculocidal, sporicidal, etc.) properties, even at relatively low concentrations. Unfortunately, however, peracids and peroxides have a relatively high energy state and tend to readily decompose while in solution. The instability of these components is compounded when incorporated into other materials, such as wet wipes. The present inventors believe, for instance, that the reductive potential of cellulose, hemicellulose, and lignin may actually cause cellulose-based materials to accelerate the degradation of peracids and peroxides in a germicidal solution. As such, a need currently exists for a technique of incorporating a germicidal solution into a wipe so that it exhibits highly effective germicidal properties and remains stable.

SUMMARY OF THE INVENTION

In accordance with one embodiment of the present invention, a disinfectant wet wipe is disclosed that comprises a nonwoven web material that is generally hydrophobic and contains a synthetic, melt-extrudable polymer. The wipe also comprises a germicidal solution that is present in an amount of from about 150 wt. % to about 1000 wt. %, based on the dry weight of the nonwoven web material. The germicidal solution contains from about 0.01 wt. % to about 2 wt. % of at least one peracid, from about 0.5 wt. % to about 15 wt. % of at least one peroxide, and from about 0.001 wt. % to about 2 wt. % of at least one surfactant.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGURE in which:

FIG. 1 is a schematic illustration of one embodiment for forming a meltblown web for use in the wet wipe of the present invention.

DETAILED DESCRIPTION OF REPRESENTATIVE EMBODIMENTS

Definitions

As used herein the term "nonwoven web" generally refers to a web having a structure of individual fibers or threads which are interlaid, but not in an identifiable manner as in a knitted fabric. Examples of suitable nonwoven webs include, but are not limited to, meltblown webs, spunbond webs, bonded carded webs, and so forth.

As used herein, the term "meltblown web" generally refers to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a disinfectant wet wipe that contains a germicidal solution and a nonwoven web material. The germicidal solution includes a peracid and peroxide, which can act synergistically together to be efficacious against pathogens when exposed thereto. To stabilize the solution over a period of time (e.g., during storage), a variety of aspects of the wipe are selectively controlled in accordance with the present invention. For example, the nonwoven web material used in the wipe is formed from a synthetic polymer and is relatively hydrophobic in nature. Without intending to be limited by theory, it is believed that such materials possess a lower reduction potential for peroxides/peracids than cellulosic-based materials. In this manner, significant degradation of the peroxide or peracid contained in the germicidal solution is limited. To improve the wettability of the nonwoven web material, one or more surfactants are also employed in the germicidal solution. Besides improving wettability, the present inventors have surprisingly discovered that certain surfactants may also improve the stability of the solution.

Various embodiments of the present invention will now be described in more detail.

I. Germicidal Solution

A. Organic Peracid

The organic peracid employed in the germicidal solution is a peroxide derivative of one or more carboxylic acids. Suitable organic peracids may include, for instance, $C_1$-$C_9$ peracids, and particularly $C_1$-$C_5$ peracids. Examples of such peracids include performic acid, peracetic acid, perbenzoic, perpropionic acid, pernonanoic acid and halogen-substituted peracids, such as monochloroperacetic acid, dichloroperacetic acid, trichloroperacetic acid trifluoroperacetic acid, metachloroperoxybenzoic acid, as well as mixtures of the foregoing, and so forth.

B. Peroxide

In addition to a peracid, the germicidal solution also contains hydrogen peroxide or another peroxide capable of releasing hydrogen peroxide when present in the solution. Suitable hydrogen peroxide sources may include, for example, peroxides of alkali and alkaline earth metals, organic peroxy compounds, pharmaceutically-acceptable salts thereof, and mixtures thereof. Peroxides of alkali and, alkaline earth metals include lithium peroxide, potassium peroxide, sodium peroxide, magnesium peroxide, calcium peroxide, barium peroxide, and mixtures thereof. Organic peroxy complexes may include carbamide peroxide (also known as urea peroxide), alkyl and/or aryl peroxides (e.g., tert-butyl peroxide, diphenyl peroxide, etc.), alkyl and/or aryl ketone peroxides (e.g., benzyol peroxide), peroxy esters, diacyl peroxides, mixtures thereof, and so forth.

The content of peroxides in the germicidal solution is typically from about 0.5 wt. % to about 15 wt. %, in some embodiments from about 1 to about 10 wt. %, in some embodiments from about 2 wt. % to about 8 wt. %, and in some embodiments, from about 3 wt. % to about 6 wt. %. Likewise, the content of peracids is typically from about 0.01 wt. % to about 2 wt. %, in some embodiments from about 0.05 to about 1 wt. %, and in some embodiments from about 0.1 wt. % to about 0.5 wt. %. It should be understood that the above concentrations are the initial concentrations immediately following formation of the solution. Because peracids and peroxides can decompose in water, however, their concentration may vary over time. For example, urea peroxide decomposes into urea and hydrogen peroxide in an aqueous solution. The hydrogen peroxide may further decompose into water and oxygen. Likewise, peracetic acid may react with water in the solution to form acetic acid and hydrogen peroxide. Nevertheless, one benefit of the present invention is that the peroxide and peracid may be sufficiently stabilized in equilibrium so that their content may be maintained at substantially the same level over a certain period of time. For example, the hydrogen peroxide content after being aged at room temperature (~25° C.) for 30 days may still be from about 0.5 wt. % to about 15 wt. %, in some embodiments from about 1 to about 10 wt. %, in some embodiments from about 2 wt. % to about 8 wt. %, and in some embodiments, from about 3 wt. % to about 6 wt. %. Similarly, the peracid content after being aged at room temperature (~25° C.) for 30 days may be from about 0.01 wt. % to about 2 wt. %, in some embodiments from about 0.05 to about 1 wt. %, and in some embodiments from about 0.1 wt. % to about 0.5 wt. %.

C. Surfactant

The germicidal solution of the present invention also includes at least one surfactant for increasing the wettability of the nonwoven web material. Generally, any surfactant may be employed that improves wettability without interacting with the hydrogen peroxide or peracid in the solution to such an extent that the stability of the solution is significantly affected.

Because nonionic surfactants generally lack formally charged negative or positive ionic groups that can react with peroxides, it is sometimes desirable to employ such surfactants in the germicidal solution. Nonionic surfactants typically have a hydrophobic base, such as a long chain alkyl group or an alkylated aryl group, and a hydrophilic chain containing a certain number (e.g., 1 to about 30) of ethoxy and/or propoxy moieties. Suitable nonionic surfactants may include, for instance, alkyl polysaccharides, block copolymers, castor oil ethoxylates, ceteoleath alcohol ethoxylates, ceteareth alcohol ethoxylates, decyl alcohol ethoxylates, dinoyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, mono-branched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tallow oil fatty acid ethoxylates, tallow amine ethoxylates, tridecanol ethoxylates, polyoxyethylene sorbitols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the TWEEN® range of polyoxyethylene surfactants available from Croda Uniqema of New Castle, Del. and the TRITON® range of polyoxyethylene surfactants (e.g., TRITON® X-100) available from Dow Chemical Co. of Midland, Mich.

Alkyl glycoside nonionic surfactants may also be employed that are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543, which are incorporated herein in their entirety by reference thereto for all purposes, describe alkyl glycosides and/or methods for their preparation. Commercially available examples of suitable alkyl glycosides include Glucopon™ 220, 225, 425, 600 and 625, all of which are available from Cognis Corp. of Cincinnati, Ohio. These products are mixtures of alkyl mono- and oligoglucopyranosides with alkyl groups based on fatty alcohols derived from coconut and/or palm kernel oil. Glucopon™ 220, 225 and 425 are examples of particularly suitable alkyl polyglycosides. Glucopon™ 220 is an alkyl polyglycoside that contains an average of 1.4 glucosyl residues per molecule and a mixture of 8 and 10 carbon alkyl groups (average carbons per alkyl chain-9.1). Glucopon™ 225 is a related alkyl polyglycoside with linear alkyl groups having 8 or 10 carbon atoms (average alkyl chain-9.1 carbon atoms) in the alkyl chain. Glucopon™ 425 includes a mixture of alkyl polyglycosides that individually include an alkyl group with 8, 10, 12, 14 or 16 carbon atoms (average alkyl chain-10.3 carbon atoms). Glucopon™ 600 includes a mixture of alkyl polyglycosides that individually include an alkyl group with 12, 14 or 16 carbon atoms (average alkyl chain 12.8 carbon atoms). Glucopon™ 625 includes a mixture of alkyl polyglycosides that individually include an alkyl group having 12, 14 or 18 carbon atoms (average alkyl chain 12.8 carbon atoms). Still other suitable alkyl glycosides are available from Dow Chemical Co. of Midland, Mich. under the TRITON® designation, e.g., TRITON® CG-110 and BG-10.

Although less likely to react with peroxides, nonionic surfactants are not necessarily as effective in enhancing the wettability of the nonwoven web material, which can result in a reduced amount of peroxide/peracid on the wipe and, in turn, decreased germicidal performance during use. Thus, in certain embodiments of the present invention, one or more ionic surfactants (e.g., cationic, anionic, zwitterionic, amphoteric, etc.) may be employed in the germicidal solution, either alone or in conjunction with one or more nonionic surfactants. As indicated above, such surfactants are generally chosen in such a manner so that they do not substantially react with the peracid/peroxide in the germicidal solution. In this regard, the present inventors have discovered that dialkyl sulfosuccinate anionic surfactants having the following formula are particularly effective for use in the present invention:

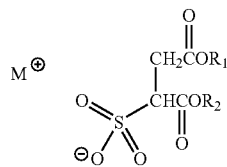

wherein, $R_1$ and $R_2$ may each independently be any straight-chain or branched alkyl group having between 3 and 22 carbon atoms, such as propyl, butyl, pentyl, hexyl, heptyl, octyl, nonyl, decyl, undecyl, dodecyl tridecyl, tetradecyl, pentadecyl, and structural isomers of the foregoing. In one particular embodiment, both $R_1$ and $R_2$ are octyl groups. As noted, the sulfosuccinate portion of the structure above exists in an anionic form, and charge neutrality is provided by the inclusion of a species M+. The species M+ may be any chemical species capable of providing a positive charge, such as alkali metals, alkaline earth metals, ammonium ions, alkylammonium ions, etc. According to one synthesis route for these materials, the dialkyl sulfosuccinic acid is first produced, then reacted with a selected alkaline substance to provide the anionic form of the sulfosuccinate. Thus, any alkaline substance that is capable of reacting with a dialkyl sulfosuccinate to provide the sulfosuccinate in its anionic form is suitable to provide a cationic species defined by M+. Particular examples of such salts include sodium dicyclohexyl sulfosuccinate and disodium isodecyl sulfosuccinate. One suitable commercially available sodium dioctyl sulfosuccinate is available from Cytec Industries, Inc. under the designation AEROSOL OT-75.

Still other suitable anionic surfactants may include, for instance, phosphate esters, alkyl sulfates, alkyl ether sulfates, alkyl ether sulfonates, sulfate esters of an alkylphenoxy polyoxyethylene ethanol, alpha-olefin sulfonates, β-alkoxy alkane sulfonates, alkylauryl sulfonates, alkyl monoglyceride sulfates, alkyl monoglyceride sulfonates, alkyl carbonates, alkyl ether carboxylates, sarcosinates, octoxynol or nonoxynol phosphates, taurates, fatty acid taurides, fatty acid amide polyoxyethylene sulfates, isethionates, or mixtures thereof. Particular examples include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkylamine oxides, $C_8$-$C_{18}$ alkyl sarcosinates, $C_8$-$C_{18}$ sulfoacetates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group can be straight chain (e.g., lauryl) or branched (e.g., 2-ethylhexyl). The cation of the anionic surfactant can be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri). Specific examples of such anionic surfactants include lauryl sulfates, octyl sulfates, 2-ethylhexyl sulfates, decyl sulfates, cocoates, lauroyl sarcosinates, linear $C_{10}$ diphenyl oxide disulfonates, lauryl ether sulfates (1 and 2 moles ethylene oxide), myristyl sulfates, oleates, stearates, tallates, ricinoleates, cetyl sulfates, and similar surfactants.

Phosphate ester surfactants may be employed, for instance, that are mono- and di-phosphate esters of nonyl phenol ethoxylate, phosphate esters of tridecyl alcohol ethoxylate, phosphate esters of isodecyl ethoxylate, and other phosphate esters of aromatic ethoxylates and aliphatic ethoxylates, phosphate esters of $C_{10}$-$C_{16}$ alkyl ethoxylates/propoxylates, etc., and mixtures thereof. Non-limiting examples of other suitable phosphates having at least one phosphorus acid group and salts thereof include phosphorous-containing acids (e.g., phosphoric acid, phosphorous acid, hypophosphorous acid, orthophosphoric acid, pyrophosphoric acid, tripolyphosphoric acid, and metaphosphoric acid), monomethyl phosphate, monoethyl phosphate, mono n-butyl phosphate, dimethyl phosphate, diethyl phosphate, ethyl ester of phosphorous acid, and other esters of phosphorous-containing acids; etc., and mixtures thereof. Other examples of such surfactants are described in U.S. Patent No. 2006/0047062 to Hsu, et al., which is incorporated herein its entirety by reference thereto for all purposes. Commercially available products include Rhodafac® PE-510, RE-410, RE-610, RE-960, RK-500A, RS-410, RS-610, RS-610A-25, RS-710, and RS-960 from Rhodia Inc.; Dextrol™ OC-110, OC-15, OC-40, OC-60, and OC-70 from Hercules, Inc. of Wilmington, Del.; Tryfac® 5553 and 5570 from Cognis Corporation; Klearfac® AA 270, Lutensit® and Maphos® from BASF Corporation; etc., and mixtures thereof.

Amphoteric surfactants may also be employed, such as derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine. Additional classes of amphoteric surfactants include phosphobetaines and the phosphitaines. For instance, some examples of such amphoteric surfactants include, but are not limited to, sodium cocoyl N-methyl taurate, sodium oleyl N-methyl taurate, sodium tall oil acid N-methyl taurate, sodium paimitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethyl betaine, cocoamidodimethylpropylsultaine, stearylamidodimethylpropylsultaine, laurylamido-bis-(2-hydroxyethyl)propylsultaine, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

Cationic surfactants may also be employed in the present invention, such as quaternary ammonium compounds (e.g., cetyl trimethyl ammonium chloride, benzalkonium chloride, benzethonium chloride, quaternium-18, stearalkonium chloride, cocotrimonium methosulfate, PEG-2 cocomonium chloride, and PEG-3 dioleoylamidoethylmonium methosulfate, etc).

The total amount of surfactants in the germicidal solution is typically from about 0.001% to about 2% by weight, in some embodiments from about 0.002% to about 1% by weight, and in some embodiments, from about 0.005% to about 0.5% by weight of the germicidal solution. Although any surfactant may generally be utilized, the germicidal solution of the present invention may contain at least one nonionic surfactant as described above. When employed, such nonionic surfactants may constitute from about 0.001% to about 0.5% by weight, in some embodiments from about 0.002% to about 0.2% by weight, and in some embodiments, from about 0.005% to about 0.1% by weight of the germicidal solution. Likewise, anionic surfactants (e.g., dialkyl sulfosuccinates, phosphate esters, etc.) may constitute from about 0.001% to about 0.5% by weight, in some embodiments from about 0.002% to about 0.2% by weight, and in some embodiments, from about 0.001% to about 0.1% by weight of the germicidal solution.

D. Other Components

In addition to those noted above, the germicidal solution may also contain a variety of other components. For example, one or more carboxylic acids may be employed in the solution in an amount effective to establish equilibrium with the peracid. Although the amount may vary, such acids are typically present in an amount of from about 0.5 wt. % to about 15 wt. %, in some embodiments from about 1 to about 10 wt. %, in some embodiments from about 2 wt. % to about 8 wt. %, and in some embodiments, from about 3 wt. % to about 6 wt. % of the solution. The carboxylic acid is generally the base acid from which the peracid was derived. Suitable acids may include, for instance, $C_1$-$C_9$ carboxylic acids, and particularly $C_1$-$C_5$ carboxylic acids. Examples of such acids include formic acid, acetic acid, benzoic, propionic acid, nonanoic acid and halogen-substituted acids, such as monochloroacetic acid, dichloroacetic acid, trichloroacetic acid trifluoroacetic acid, meta-chlorobenzoic acid, as well as mixtures of the foregoing, and so forth. If desired, salts of acids may also be employed. In one particular embodiment, acetic acid is employed to establish equilibrium with peracetic acid.

Water-soluble polymers may also be employed for adjusting the rheological properties of the solution and enhancing its overall efficacy. Such polymers may be employed, for instance, in an amount of from 0.1% to 1%. Particularly suitable polymers are vinyl polymers containing a lactam group (e.g., polyvinylpyrrolidone). Such polymers are described in more detail WO 2006/076334 to Martin. et al. and U.S. Patent Application Publication No. 2006/0229225 to Martin, et al., both of which are incorporated herein in their entirety by reference thereto for all purposes.

Because the germicidal solution may be exposed to metallic impurities (e.g., calcium ions in water) during use, a metal chelating agent may be employed in the solution, such as in an amount from about 0.05 wt. % to about 10 wt. %, in some embodiments from about 0.1 wt. % to about 5 wt. %, and in some embodiments, from about 0.5 wt. % to about 4 wt. % of the germicidal solution. Without being limited by theory, it is believed that the metal chelating agent may regulate the exposure of the peroxide to such metal ions and thereby limit the premature release of active peroxide. The chelating agent may include, for instance, aminocarboxylic acids (e.g., ethylenediaminetetraacetic acid) and salts thereof, hydroxycarboxylic acids (e.g., citric acid, tartaric acid, ascorbic acid, etc.) and salts thereof, polyphosphoric acids (e.g., tripolyphosphoric acid, hexametaphosphoric acid, etc.) and salts thereof, cyclodextrin, and so forth. Desirably, the chelating agent is capable of forming multiple coordination complexes with metal ions to reduce the likelihood that any of the free metal ions will interact with the peroxide. In one embodiment, for example, a chelating agent containing two or more aminodiacetic acid groups or salts thereof may be utilized. Aminodiacetic acid groups generally have the following structure:

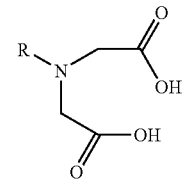

One example of such a chelating agent is ethylenediaminetetraacetic acid (EDTA). Examples of suitable EDTA salts include calcium-disodium EDTA, diammonium EDTA, disodium and dipotassium EDTA, triethanolamine EDTA, trisodium and tripotassium EDTA, tetrasodium and tetrapotassium EDTA. Still other examples of similar aminodiacetic acid-based chelating agents include, but are not limited to, butylenediaminetetraacetic acid, 1,2-cyclohexylenediaminetetraacetic acid (CyDTA), diethylenetriaminepentaacetic acid, ethylenediaminetetrapropionic acid, (hydroxyethyl) ethylenediaminetriacetic acid (HEDTA), N N,N',N'-ethylenediaminetetra(methylenephosphonic)acid (EDTMP), triethylenetetraminehexaacetic acid (TTHA), 1,3-diamino-2-hydroxypropane-N,N,N',N'-tetraacetic acid (DHPTA), methyliminodiacetic acid, propylenediaminetetraacetic acid, and so forth.

Besides those mentioned above, the germicidal solution of the present invention may also contain a variety of other optional ingredients. For example, the germicidal solution may contain a preservative or preservative system to inhibit the growth of pathogens over an extended period of time. Suitable preservatives for use in the germicidal solution may include, for instance, Kathon CG®, which is a mixture of methylchloroisothiazolinone and methylisothiazolinone available from Rohm & Haas; Neolone 950®, which is methylisothiazolinone available from Rohm & Haas, Mackstat H 66 (available from McIntyre Group, Chicago, Ill.); DMDM hydantoin (e.g., Glydant Plus, Lonza, Inc., Fair Lawn, N.J.); iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; imidazolidinyl urea; diazolidinyl urea; and the like. Still other preservatives may include ethylhexylglycerin (Sensiva SC 50 by Schulke & Mayr), phenoxyethanol (Phenoxyethanol by Tri-K Industries), caprylyl glycol (Lexgard O by Inolex Chemical Company, Symdiol 68T (a blend of 1,2-hexanediol, caprylyl glycol and tropolone by Symrise) and Symocide PT (a blend of phenoxyethanol and tropolone by Symrise).

The germicidal solution may also include various other components as is well known in the art, such as binders, colorants, electrolytic salts, pH adjusters, fragrances, etc. Various other possible ingredients may be described in U.S. Pat. Nos. 5,681,380 to Nohr, et al. and 6,524,379 to Nohr, et al., which are incorporated herein in their entirety by reference thereto for all purposes.

To form the germicidal solution, one or more of the components may typically be dissolved or dispersed in a solvent (e.g., water). For example, one or more of the above-mentioned components may be mixed with the solvent, either sequentially or simultaneously, to form the germicidal solution. Although the actual concentration of the solvent employed will generally depend on the nature of the germicidal solution and its components, it is nonetheless typically present in an amount from about 50 wt. % to about 99.9 wt. %, in some embodiments from about 60 wt. % to about 99 wt. %, and in some embodiments, from about 75 wt. % to about 98 wt. % of the germicidal solution.

While it may be desirable to mix together the organic peracid, peroxide, and surfactant prior to incorporating the solution into the wipe, it should be understood that certain components of the solution may instead be added after formation of the wipe. In one embodiment, for instance, a wipe may be initially formed that contains the aforementioned surfactant. This wipe may then be packaged and provided to a user who subsequently adds, for example, the organic peracid and/or peroxide to form the germicidal solution of the present invention.

II. Wipe

The wipe of the present invention includes a nonwoven web material is generally hydrophobic in nature and is formed from a melt-extrudable, synthetic polymer. Examples of such polymers may include, for instance, polyolefins, such as polyethylene, such as high density polyethylene, medium density polyethylene, low density polyethylene, and linear low density polyethylene; polypropylene, such as isotactic polypropylene, atactic polypropylene, and syndiotactic polypropylene; polybutylene, such as poly(1-butene) and poly(2-butene); polypentene, such as poly(1-pentene) and poly(2-pentene); poly(3-methyl-1-pentene); poly(4-methyl-1-pentene); and copolymers and blends thereof. Suitable copolymers include random and block copolymers prepared from two or more different unsaturated olefin monomers, such as ethylene/propylene and ethylene/butylene copolymers. If desired, elastomeric polymers may also be used, such as elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety and B is an elastomeric polymer midblock, such as a conjugated diene or a lower alkene polymer. Such copolymers may include, for instance, styrene-isoprene-styrene (S-I-S), styrene-butadiene-styrene (S-B-S), styrene-ethylene-butylene-styrene (S-EB-S), styrene-isoprene (S-I), styrene-butadiene (S-B), and so forth. Commercially available A-B-A' and A-B-A-B copolymers include several different S-EB-S formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and from Dow Chemical Co. of Midland, Mich. under the name AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. Nos. 5,539,056 to Yang, et al. and 5,596,052 to Resconi, et al., which are incorporated herein in their entirety by reference thereto for all purposes.

Any of a variety of processes may be used to form the nonwoven web material. Referring to FIG. 1, for example, one embodiment of a method for forming a meltblown web is shown. Meltblown webs have a small average pore size, which may be used to inhibit the passage of liquids and particles, while allowing gases (e.g., air and water vapor) to pass therethrough. To achieve the desired pore size, the meltblown fibers are typically "microfibers" in that they have an average size of 10 micrometers or less, in some embodiments about 7 micrometers or less, and in some embodiments, about 5 micrometers or less. The ability to produce such fine fibers may be facilitated in the present invention through the use of a thermoplastic composition having the desirable combination of low apparent viscosity and high melt flow rate.

In FIG. 1, for instance, the raw materials (e.g., polymer, opacifying agent, carrier resin, etc.) are fed into an extruder 12 from a hopper 10. The raw materials may be provided to the hopper 10 using any conventional technique and in any state. The extruder 12 is driven by a motor 11 and heated to a temperature sufficient to extrude the melted polymer. For example, the extruder 12 may employ one or multiple zones operating at a temperature of from about 50° C. to about 500° C., in some embodiments, from about 100° C. to about 400° C., and in some embodiments, from about 150° C. to about 250° C. Typical shear rates range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. If desired, the extruder may also possess one or more zones that remove excess moisture from the polymer, such as vacuum zones, etc. The extruder may also be vented to allow volatile gases to escape.

Once formed, the thermoplastic composition may be subsequently fed to another extruder in a fiber formation line (e.g., extruder 12 of a meltblown spinning line). Alternatively, the thermoplastic composition may be directly formed into a fiber through supply to a die 14, which may be heated by a heater 16. It should be understood that other meltblown die tips may also be employed. As the polymer exits the die 14 at an orifice 19, high pressure fluid (e.g., heated air) supplied by conduits 13 attenuates and spreads the polymer stream into microfibers 18.

The microfibers 18 are randomly deposited onto a foraminous surface 20 (driven by rolls 21 and 23) with the aid of an optional suction box 15 to form a meltblown web 22. The distance between the die tip and the foraminous surface 20 is generally small to improve the uniformity of the fiber laydown. For example, the distance may be from about 1 to about 35 centimeters, and in some embodiments, from about 2.5 to about 15 centimeters. In FIG. 1, the direction of the arrow 28 shows the direction in which the web is formed (i.e., "machine direction") and arrow 30 shows a direction perpendicular to the machine direction (i.e., "cross-machine direction"). Optionally, the meltblown web 22 may then be compressed by rolls 24 and 26. The desired denier of the fibers may vary depending on the desired application. Typically, the fibers are formed to have a denier per filament (i.e., the unit of linear density equal to the mass in grams per 9000 meters of fiber) of less than about 6, in some embodiments less than about 3, and in some embodiments, from about 0.5 to about 3. In addition, the fibers generally have an average diameter of from about 0.1 to about 20 micrometers, in some embodiments from about 0.5 to about 15 micrometers, and in some embodiments, from about 1 to about 10 micrometers.

Once formed, the nonwoven web may then be bonded using any conventional technique, such as with an adhesive or autogenously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with the polymers used to form the fibers. Suitable autogenous bonding techniques may include ultrasonic bonding, thermal bonding, through-air bonding, calendar bonding, and so forth. For example, the web may be further bonded or embossed with a pattern by a thermo-mechanical process in which the web is passed between a heated smooth anvil roll and a heated pattern roll. The pattern roll may have any raised pattern which provides the desired web properties or appearance. Desirably, the pattern roll defines a raised pattern which defines a plurality of bond locations which define a bond area between about 2% and 30% of the total area of the roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., as well as U.S. Design Pat. Nos. 428,267 to Romano et al.; 390,708 to Brown; 418,305 to Zander, et al.; 384,508 to Zander, et al.; 384,819 to Zander, et al.; 358,035 to Zander, et al.; and 315,990 to Blenke, et al., all of which are incorporated herein in their entirety by reference thereto for all purposes. The pressure between the rolls may be from about 5 to about 2000 pounds per lineal inch. The pressure between the rolls and the temperature of the rolls is balanced to obtain desired web properties or appearance while maintaining cloth like properties. As is well known to those skilled in the art, the temperature and pressure required may vary depending upon many factors including but not limited to, pattern bond area, polymer properties, fiber properties and nonwoven properties.

In addition to meltblown webs, a variety of other nonwoven webs may also be formed from the thermoplastic composition, such as spunbond webs, bonded carded webs, etc. For example, the polymer may be extruded through a spinnerette, quenched and drawn into substantially continuous filaments, and randomly deposited onto a forming surface. Alternatively, the polymer may be formed into a carded web by placing bales of fibers formed from the thermoplastic composition into a picker that separates the fibers. Next, the fibers are sent through a combing or carding unit that further breaks apart and aligns the fibers in the machine direction so as to form a machine direction-oriented fibrous nonwoven web. Once formed, the nonwoven web is typically stabilized by one or more known bonding techniques.

If desired, the nonwoven web material may also be subjected to mechanical bonding in which the fibers are entangled with the aid of thin jets of air or liquid to provide an interlocking of the fibers and the fiber structure. This process is described in detail in U.S. Pat. No. 3,486,168 to Evans et al., which is incorporated herein in its entirety by reference thereto for all purposes. Such entangled materials (often referred to as "spunlace" materials) have pronounced textile-like properties.

The nonwoven web may also be a composite that contains a combination of the thermoplastic composition fibers and other types of fibers (e.g., staple fibers, filaments, etc). For example, additional synthetic staple fibers may be utilized, such as those formed from polyolefins, e.g., polyethylene, polypropylene, polybutylene, and so forth. The nonwoven web material may also have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. Nos. 4,041,203 to Brock et al.; 5,213,881 to Timmons, et al.; 5,464,688 to Timmons, et al.; 4,374,888 to Bornslaeger; 5,169,706 to Collier, et al.; and 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Regardless of the materials or processes utilized to form the wipe, the basis weight of the wipe is typically from about 10 to about 200 grams per square meter (gsm), and in some embodiments, between about 20 to about 100 gsm. Lower basis weight products may be particularly well suited for use as light duty wipes, while higher basis weight products may be better adapted for use as industrial wipes. The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 40.0 centimeters. The wipes may likewise have an unfolded width of from about 2.0 to about 80.0 centimeters, and in some embodiments, from about 10.0 to about 40.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. Nos. 5,785,179 to Buczwinski, et al.; 5,964,351 to Zander; 6,030,331 to Zander; 6,158,614 to Haynes, et al.; 6,269,969 to Huang, et al.; 6,269,970 to Huang, et al.; and 6,273,359 to Newman, et al., which are incorporated herein in their entirety by reference thereto for all purposes.

The germicidal solution may be applied to the wipe using any suitable method known in the art, such as spraying, dipping, saturating, impregnating, brush coating, and so forth. The amount of the germicidal solution employed may depend upon the type of wipe material utilized, the type of container used to store the wipes, the nature of the cleaning formulation, and the desired end use of the wipes. Generally, each wipe contains from about 150 wt. % to about 1000 wt. %, in some embodiments from about 250 wt. % to about 750 wt. %, and in some embodiments, from about 300 wt. % to about 600 wt. % of a germicidal solution based on the dry weight of the nonwoven web material used to form the wipe.

The disinfectant wipe of the present invention may be used to disinfectant and/or sanitize any surface (e.g., food service counters, tables, medical instruments, high touch surfaces, bathroom counters, toilets, laboratory benches, bed rails, telephones, doorknobs, etc.). As indicated above, the present inventors have discovered that the stability of the germicidal solution and wettability of the wipe may be enhanced through selective control over the components employed in the germicidal solution and their relative amounts, as well as over the nature of the wipe itself. By maximizing both stability and wettability in this manner, the disinfectant wipe may effectively be efficacious against (e.g., reduce by a measurable amount or to destroy entirely) a broad spectrum of pathogens when exposed thereof. Examples of pathogens that may be inhibited include bacteria (including cyanobacteria, Mycobacteria, and bacterial spores), lichens, microfungi, protozoa, virinos, viroids, viruses, fungi (e.g., molds and yeast), and some algae. For example, the wipe may be efficacious against several medically significant bacteria groups, such as gram negative rods (e.g., *Entereobacteria*); gram negative curved rods (e.g., *Heliobacter, Campylobacter*, etc.); gram negative cocci (e.g., *Neisseria*); gram positive rods (e.g., *Bacillus, Clostridium*, etc.); gram positive cocci (e.g., *Staphylococcus, Streptococcus*, etc.); obligate intracellular parasites (e.g., *Rickettsia* and *Chlamydia*); acid fast rods (e.g., *Mycobacterium, Nocardia*, etc.); spirochetes (e.g., *Treponema, Borellia*, etc.); and mycoplasmas (i.e., tiny bacteria that lack a cell wall). Particular species of bacteria that may be inhibited include *Escherichia coli* (gram negative rod), *Klebsiella pneumonia* (gram negative rod), *Streptococcus* (gram positive cocci), *Salmonella choleraesuis* (gram negative rod), *Staphyloccus aureus* (gram positive cocci), and *Psuedomonas aeruginosa* (gram negative rod). In addition to bacteria, other pathogens of interest include molds (e.g., *Aspergillus niger*), yeasts (e.g., *Candida albicans*), which belong to the Fungi kingdom, and viruses, such as lipid (HIV, RSV) and non-lipid (Polio, Rhinovirus, Norovirus, Hepatitis A) viruses.

Upon exposure for a certain period of time, the disinfectant wipe may provide a log reduction of at least about 2, in some embodiments at least about 3, in some embodiments at least about 4, and in some embodiments, at least about 5 (e.g., about 6). Log reduction, for example, may be determined from the % population killed by the composition according to the following correlations:

| % Reduction | Log Reduction |
|---|---|
| 90 | 1 |
| 99 | 2 |
| 99.9 | 3 |
| 99.99 | 4 |
| 99.999 | 5 |
| 99.9999 | 6 |

Such a log reduction may be achieved in accordance with the present invention after only a relatively short exposure time. For example, the desired log reduction may be achieved after exposure for only 30 minutes, in some embodiments 10 minutes, and in some embodiments, 5 minutes, in other embodiments 1 minute, and in some embodiments down to 15 seconds.

The present invention may be better understood with reference to the following example.

EXAMPLE

A series of pre-saturated wipe samples were produced with treated polypropylene fibrous meltblown sheets and saturated with a solution containing approximately 4.3% hydrogen peroxide and 0.20% peracetic acid. Nonwoven substrate treatments included no treatment, a mixture of a cationic surfactant (quaternary ammonium compound) and a nonionic surfactant, and a mixture containing a non-ionic surfactant and an anionic surfactant, a nonionic surfactant, and an anionic surfactant. For comparison, a cellulosic basesheet was also incorporated. Nonwoven substrate samples were saturated with 500% solution by weight in the case of polypropylene and 350% by weight in the case of cellulose. Samples were then placed in conditioned high-density polyethylene (HDPE) containers and kept at either room temperature storage or in an oven held at 40° C. for 14 to 30 days. An aliquot of the solution was used as a control and kept in the same conditions. The results are shown below.

| Example | Wipe Material | Treatment | Stability Results |
|---|---|---|---|
| 1 | Commercially-available 54gsm HYDROKNIT* Material (manufactured by Kimberly-Clark Professional), comprised of ~30% (by weight) polypropylene spunbond and ~70% cellulose | None | Not stable: degradation of peracetic acid and hydrogen peroxide |

-continued

| Example | Wipe Material | Treatment | Stability Results |
|---|---|---|---|
| 2 | 2.5 osy polypropylene meltblown made by Kimberly-Clark | None | Not stable: degradation of peracetic acid and hydrogen peroxide |
| 3 | Treated 1.0 osy polypropylene meltblown, distributed by Kimberly-Clark Professional as "KIMTECH PREP ™ Wipers for Bleach and Sanitizers" | Uniquat 22C50 (0.08 wt. %) and Glucopon (0.25 wt. %) Treatment was sprayed onto nonwoven substrate web during manufacturing process. | Not stable: degradation of peracetic acid and hydrogen peroxide |
| 4 | Treated 2.5 osy polypropylene meltblown, distributed by Kimberly-Clark Professional as "KIMTECH PURE ™ W4 Dry Wipers" | Aerosol OT-75 (0.15 wt. %) and Synthrapol KB (0.3 wt. %). Treatment was sprayed onto nonwoven substrate web during manufacturing process. | Stable |
| 5 | 1.0 osy polypropylene meltblown. | Aerosol OT-75 (0.15 wt. %) and Synthrapol KB (0.3 wt. %). Treatment was sprayed onto nonwoven substrate web during manufacturing process. | Stable |
| 6 | 1.0 osy polypropylene meltblown. | Synthrapol KB (0.5 wt. %). Treatment was applied to basesheet using "dip and squeeze" laboratory equipment. | Not stable: degradation of peracetic acid and hydrogen peroxide |
| 7 | 1.0 osy polypropylene meltblown. | Aerosol OT-75 (0.15 wt. %). Treatment was incorporated into liquid add-on. | Stable |
| 8 | 1.0 osy polypropylene meltblown | Manawet from Manufacturers Chemicals LLC (0.3 wt. %). Treatment was applied to basesheet using "dip and squeeze" laboratory equipment. | Stable |

The peracetic acid and hydrogen peroxide decomposed other than Examples 4 and 5.

Example 5 was also tested for efficacious activity against a broad spectrum of pathogens using industry-standard test methods designed to evaluate germicidal activity of pre-saturated towelettes on hard non-porous surfaces. For viruses, a quantitative virucidal activity based on an ASTM standard method was used, and for the remaining microbes, a qualitative carrier test based on AOAC methods was utilized. Shown below is a summary of microbial log reductions and/or kill and corresponding contact times demonstrated by Example 5.

| Class | Organism | Performance | Contact Time |
|---|---|---|---|
| Bacteria | Salmonella enterica Klebsiella pneumonia Escherichia coli ESBL | >4 log reduction | 30 seconds |
| Fungi | Aspergillus niger Tricophyton mentagrophytes | >4 log reduction | 1 minute |
| Mycobacteria | Mycobacterium bovis | >4 log reduction | 1 minute |
| Spores | Clostridium difficile | >6 log reduction | 5 minutes |
| Viruses: Lipid (enveloped) | Influenza A Herpes Simplex Virus (Types 1 and 2) | >3 log reduction | 30 seconds |
| Viruses: Non-lipid (Non-enveloped) | Poliovirus Feline Calicivirus (surrogate for Norovirus) | >3 log reduction | 5 minutes |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A disinfectant wet wipe comprising:
   a nonwoven web material that is generally hydrophobic and contains a synthetic, melt-extrudable polymer, wherein the nonwoven web material is generally free of cellulosic fibers; and
   a germicidal solution that is present in an amount of from about 150 wt. % to about 1000 wt. %, based on the dry weight of the nonwoven web material, wherein the germicidal solution contains from about 0.01 wt. % to about 2 wt. % of at least one peracid, from about 0.5 wt. % to about 15 wt. % of at least one peroxide, from about 0.002 wt. % to about 0.2 wt. % of an anionic surfactant, and from about 0.001 wt. % to about 0.5 wt. % of a nonionic surfactant, wherein the anionic surfactant includes a dioctyl sulfosuccinate and the nonionic surfactant includes a decyl alcohol ethoxylate.

2. The disinfectant wet wipe of claim 1, wherein the peracid includes performic acid, peracetic acid, perbenzoic acid, perpropionic acid, pernonanoic acid, monochloroperacetic acid, dichloroperacetic acid, trichloroperacetic acid trifluoroperacetic acid, meta-chloroperoxybenzoic acid, or a mixture thereof.

3. The disinfectant wet wipe of claim 1, wherein the peracid includes peracetic acid.

4. The disinfectant wet wipe of claim 1, wherein the peroxide includes hydrogen peroxide, lithium peroxide, potassium peroxide, sodium peroxide, magnesium peroxide, calcium peroxide, barium peroxide, carbamide peroxide, tert-butyl peroxide, diphenyl peroxide, benzyol peroxide, or a mixture thereof.

5. The disinfectant wet wipe of claim 1, wherein the peroxide includes hydrogen peroxide.

6. The disinfectant wet wipe of claim 1, wherein the germicidal solution contains from about 1 wt. % to about 10 wt. % of the peroxide.

7. The disinfectant wet wipe of claim 1, wherein the germicidal solution contains from about 0.05 wt. % to about 1 wt. % of the peracid.

8. The disinfectant wet wipe of claim 1, wherein the germicidal solution further comprises at least one carboxylic acid in an amount effective to establish equilibrium with the peracid.

9. The disinfectant wet wipe of claim 1, wherein the germicidal solution further comprises a metal chelating agent, preservative, fragrance, or a combination thereof.

10. The disinfectant wet wipe of claim 1, wherein water constitutes from about 75 wt. % to about 98 wt. % of the germicidal solution.

11. The disinfectant wet wipe of claim 1, wherein the germicidal solution is present in an amount from about 300 wt. % to about 600 wt. % based on the dry weight of the nonwoven web material.

12. The disinfectant wet wipe of claim 1, wherein the nonwoven web material includes a meltblown web.

13. The disinfectant wet wipe of claim 1, wherein the nonwoven web material includes a spunbond web.

14. The disinfectant wet wipe of claim 1, wherein the synthetic polymer includes a polyolefin.

15. A method for disinfecting a hard surface, the method comprising contacting the surface with a wet wipe comprising a generally hydrophobic nonwoven web material and a germicidal solution that constitutes from about 150 wt. % to about 1000 wt. % of the dry weight of the nonwoven web material, wherein the nonwoven web material is generally free of cellulosic fibers, and wherein the germicidal solution contains from about 0.01 wt. % to about 2 wt. % of at least one peracid, from about 0.5 wt. % to about 15 wt. % of at least one peroxide, 0.002 wt % to about 0.2 wt % of an anionic surfactant, and from about 0.001 wt % to about 0.5 wt % of a nonionic surfactant, wherein the anionic surfactant includes a dioctyl sulfosuccinate and the nonionic surfactant includes a decyl alcohol ethoxylate.

16. The method of claim 15, wherein the peracid includes peracetic acid and the peroxide includes hydrogen peroxide.

17. The method of claim 15, wherein the germicidal solution contains from about 1 wt. % to about 10 wt. % of the peroxide and from about 0.05 to about 1 wt. % of the peracid.

18. The method of claim 15, the surfactant includes an anionic surfactant, nonionic surfactant, or a combination thereof.

19. The method of claim 15, wherein water constitutes from about 75 wt. % to about 98 wt. % of the germicidal solution.

20. The method of claim 15, wherein the germicidal solution is present in an amount from about 300 wt. % to about 600 wt. %, based on the dry weight of the nonwoven web material.

21. The method of claim 15, wherein a log reduction of at least about 3 is achieved for at least one pathogen.

22. The disinfectant wet wipe of claim 1, wherein the nonwoven web material is a composite that includes a meltblown web in combination with synthetic staple fibers.

23. The disinfectant wet wipe of claim 1, wherein the nonwoven web material is a laminate that contains a spunbond layer and a meltblown layer.

24. The disinfectant wipe of claim 1, wherein the germicidal solution contains from about 0.05% to about 1 wt. % of the peracid and from about 2 wt. % to about 8 wt. % of the peroxide.

25. The disinfectant wipe of claim 1, wherein the germicidal solution contains from about 0.1% to about 0.5 wt. % of the peracid and from about 3 wt. % to about 6 wt. % of the peroxide.

26. The disinfectant wipe of claim 1, wherein the germicidal solution is sprayed onto the nonwoven web material.

27. The disinfectant wipe of claim 1, wherein the disinfectant wipe provides a log reduction of a pathogen of at least about 3 after 5 minutes of exposure.

* * * * *

UNITED STATES PATENT AND TRADEMARK OFFICE
CERTIFICATE OF CORRECTION

| | | |
|---|---|---|
| PATENT NO. | : 8,563,017 B2 | Page 1 of 1 |
| APPLICATION NO. | : 12/334755 | |
| DATED | : October 22, 2013 | |
| INVENTOR(S) | : Corey Thomas Cunningham et al. | |

It is certified that error appears in the above-identified patent and that said Letters Patent is hereby corrected as shown below:

In the Claims:

In Claim 2 (column 17, ll. 29)

"...trichloroperacetic acid trifluo-..." should read --...trichloroperacetic acid, trifluo...--

Signed and Sealed this
Thirty-first Day of December, 2013

Margaret A. Focarino
*Commissioner for Patents of the United States Patent and Trademark Office*